United States Patent [19]

Ohzu

[11] 4,009,940

[45] Mar. 1, 1977

[54] APPARATUS FOR PRODUCING OPTICAL INTERFERENCE PATTERN WITH CONTINUOUSLY VARIABLE FRINGE SPACING

[75] Inventor: Hitoshi Ohzu, Hino, Japan

[73] Assignee: Takata Ophthalmic Instruments Co., Ltd., Tokyo, Japan

[22] Filed: Apr. 22, 1975

[21] Appl. No.: 570,920

[30] Foreign Application Priority Data

Apr. 27, 1974   Japan .......................... 49-4904809

[52] U.S. Cl. ................................. 350/163; 351/14; 356/113
[51] Int. Cl.² ..................... G02B 27/00; A61B 3/10
[58] Field of Search .............. 350/163, 162 R, 320, 350/169–174, 299; 356/106 R, 113, 109–111; 351/13, 14; 250/550

[56] References Cited

UNITED STATES PATENTS

| | | | |
|---|---|---|---|
| 1,383,543 | 7/1921 | Ives | 350/174 |
| 1,722,356 | 7/1929 | Romer | 350/173 |
| 1,862,950 | 6/1932 | Ball | 350/173 |
| 3,507,564 | 4/1970 | Franks | 350/162 R |
| 3,586,416 | 6/1971 | DeBitetto | 350/163 |
| 3,628,866 | 12/1971 | Mueller | 350/162 R |
| 3,695,749 | 10/1972 | Stapleton | 350/163 |
| 3,832,063 | 8/1974 | Matsumoto et al. | 356/109 |

FOREIGN PATENTS OR APPLICATIONS

| | | | |
|---|---|---|---|
| 166,518 | 12/1964 | U.S.S.R. | 350/162 R |

OTHER PUBLICATIONS

Jenkins & White, *Fund of Optics*, 3rd Ed., 1957, p. 259.

*Primary Examiner*—John K. Corbin
*Assistant Examiner*—Jon W. Henry
*Attorney, Agent, or Firm*—Frank J. Jordan

[57] ABSTRACT

First and second triangular prisms are bonded together at their bases with a semi-transparent reflecting material therebetween. A light beam from a laser is incident on the upstream face of the first prism and refracted thereby so as to be incident on the semi-transparent reflecting material at a predetermined angle to the longitudinal axis thereof. One component of the beam is reflected from the semi-transparent material and refracted by the first prism so as to emerge therefrom parallel to the axis of the semi-transparent material. Another component of the beam passes through the semi-transparent material and is refracted by the second prism so as to emerge therefrom parallel to the axis of the semi-transparent material. A lens converges the two beam components to produce an interference pattern. Linear movement of the laser or a plane reflector disposed between the laser and the first prism varies the point of incidence of the beam on the upstream face of the first prism and thereby the spacing between the first and second beam components emerging from the first and second prisms and the fringe spacing of the interference pattern.

14 Claims, 6 Drawing Figures

APPARATUS FOR PRODUCING OPTICAL INTERFERENCE PATTERN WITH CONTINUOUSLY VARIABLE FRINGE SPACING

The present invention relates to apparatus for producing an optical interference pattern with a continuously variable fringe spacing.

Apparatus has recently been introduced into the field of ophthalmology for testing visual acuity by means of laser-generated interference fringe patterns. With such apparatus, an interference pattern is produced on the retina of the eye, and the fineness of the interference pattern which can be resolved by the eye gives an accurate estimation of the visual acuity of the retina. The apparatus is especially effective since the fringe pattern formed on the retinal surface by interference of light beams is not degraded by ordinary optical aberrations or refractive errors of the eye. The apparatus is ideally suited for visual acuity testing of cataract patients since it clearly establishes the extent to which a loss of visual acuity is caused by degenerative retinal disease rather than lens changes. In cataract cases, the ocular opacities appear as blank areas in the interference pattern.

In addition to cataract cases, such apparatus is also able to provide valuable information in ametropic cases such as keratoconus and irregular astigmatism. It can furthermore measure loss of visual acuity caused by medications such as "Ethanbutol" which is used in treating tuberculosis. The apparatus is compact and easy to use and can be employed by general ophthalmologists and optical establishments.

Known apparatus of this type is generally constructed in two configurations: a first type based on the Michelson interferometer principle and a second type using diffraction gratings. Both of these types are extremely difficult to align and calibrate and highly sensitive to vibrations. A usable apparatus of either type is therefore quite expensive.

It is therefore an object of the present invention to provide apparatus for producing an optical interference pattern with continuously variable fringe spacing which is simple in configuration, accurate and stable in operation and inexpensive to manufacture and maintain.

It is another object of the present invention to provide apparatus for splitting an incident light beam into first and second parallel beam components with the spacing between the beam components being continuously variable which constitutes a novel subcombination of the apparatus for producing the optical interference pattern.

It is another object of the present invention to provide apparatus for splitting an incident light beam into two parallel beam components with continuously variable spacing therebetween which comprises two prisms bonded together at their bases with a semi-transparent reflecting material disposed therebetween.

It is another object of the present invention to provide apparatus for splitting an incident light beam into two parallel beam components which comprises two plane mirrors and a semi-transparent plane mirror.

The above and other objects, features and advantages of the present invention will become clear from the following detailed description taken with the accompanying drawings, in which:

FIGS. 4a to 4c show various possible configurations of prisms in the apparatus shown in FIG. 2.

Figure 1:
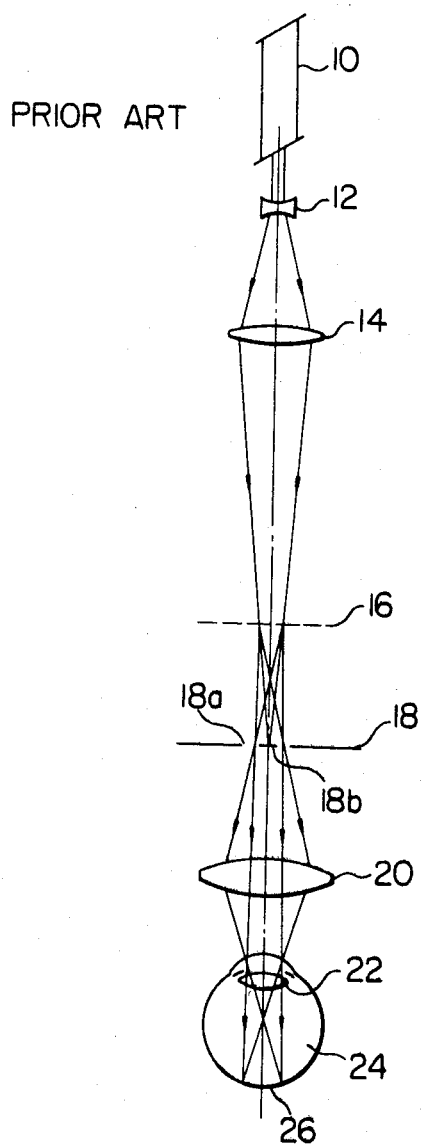
FIG. 1 is a schematic view of a prior art apparatus for producing an optical interference pattern with continuously variable fringe spacing.

Referring now to FIG. 1, a prior art apparatus comprises a laser 10 for producing a coherent light beam as shown by arrows. A diverging lens 12 diverges the laser beam which is subsequently converged by a converging lens 14 onto a diffraction grating 16. An interference pattern produced by the diffraction grating 16 is incident on a mask 18 which is formed with an aperture 18a and a central black thread 8b. The arrangement is such that the central or zero order maxima of the interference pattern is blocked by the thread 18b and the size of the aperture 18a is such that only the first order maxima, which have equal intensity, are allowed to pass through the aperture 18a on the opposite sides of the thread 18b in the form of two point sources of coherent light. These point sources are focussed by a converging lens 20 through a lens 22 of a human eye 24 onto a retina 26 of the eye 24 in such a manner as to overlap and produce a pattern of alternating light and dark stripes or fringes by interference. The spacing between the fringes which can be resolved by the retina 26 gives an accurate estimation of the retinal visual acuity. The fringe spacing can be varied by moving the diffraction grating 16 back and forth between the lens 14 and mask 18. Since this results in a variation in the spacing between the first order maxima of the interference pattern on the mask 18 and also in the size of the interference fringes, the size of the aperture 18a must be varied by means of, for example, an iris diaphragm which is not shown, and the mask 18 must be moved back and forth between the diffraction grating 16 and the lens 20 in a specific relationship with the position of the diffraction grating 16.

The apparatus shown in FIG. 1 suffers from the following and other drawbacks.

1. It is very difficult to produce and maintain the proper alignment and calibration between the various components of the apparatus, especially since it is necessary to move the diffraction grating 16 and mask 18 and vary the size of the aperture 18a for each required value of fringe spacing.

2. The apparatus is complicated in configuration and highly expensive to manufacture with sufficient accuracy.

3. The shock and vibration resistance is very low.

4. The light loss is great.

5. A highly accurate and expensive diffraction grating is necessary to produce an interference pattern which is usable in practical applications.

6. A large amount of displacement of the diffraction grating is required to produce sufficient practical variation in the fringe spacing. The apparatus is therefore quite large in size and represents inefficient use of space.

Figure 2:
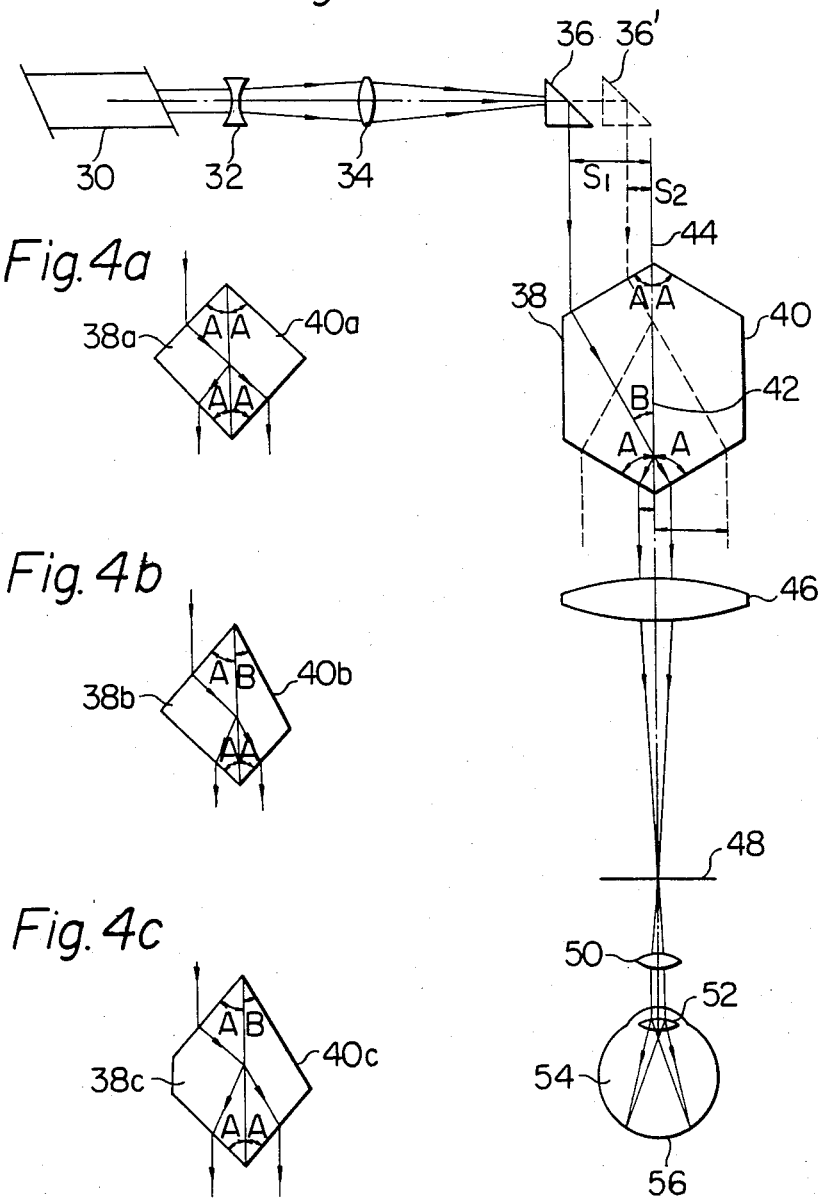
FIG. 2 is a schematic view of apparatus embodying the present invention for producing an optical interference pattern with continuously variable fringe spacing and comprising novel means for splitting an incident light beam into two parallel beam components with continuously variable spacing therebetween.

The apparatus of the present invention which is shown in FIG. 2 overcomes all of these drawbacks by the application of a novel continuously variable beam splitting means which does not comprise a diffraction grating. The apparatus may be applied not only to the field of ophthalmology but to many industrial applications in which an interference pattern with continuously variable fringe spacing is required such as for testing television camera tubes or photographic films.

The apparatus of FIG. 2 comprises a laser 30 as a coherent light beam source which radiates a coherent light beam as shown by arrows. A diverging lens 32 and converging lens 34 are provided to converge the beam onto a plane reflector here shown as a right angle prism 36. Prisms 38 and 40 of identical truncated triangular cross-section, index of refraction and face angles A are joined at their bases with a semi-transparent reflecting material 42 disposed therebetween. The bases of the prisms 38 and 40 are parallel to a longitudinal axis of the material 42 which is designated as 44. A converging lens 46 is disposed downstream of the prisms 38 and 40 to form an interference pattern at a focal plane 48 as will be described below. An objective lens 50 disposed downstream of the converging lens 46 is provided to focus an image of the interference pattern through a lens 52 of a human eye 54 onto a retina 56 of the eye 54.

In operation, the beam from the laser 30 is refracted by the diverging lens 32 and converging lens 34 to produce a narrow beam which is incident on the prism 36. With the prism 36 in the position shown in solid line, the beam transverses a path which is shown by solid arrows in the figure.

The beam reflected from the prism 36 is incident on the upper face (as shown in FIG. 2) of the prism 38 and is refracted by the prism 38 so as to be incident on the axis 44 of the semi-transparent reflecting material 42 at an angle B. The transmittance and reflectance of the material 42 are preferably equal at the incident angle B. One component of the beam is reflected from the material 42 and travels through the prism 38 to the bottom face thereof. At the bottom face of the prism 38 the beam component is refracted into a beam path which is parallel to the axis 44 and oriented to the left thereof as shown in FIG. 2.

A second beam component passes through the material 42 and travels through the prism 40 to the bottom face thereof, from which it is refracted into a second beam path parallel to the axis 44 and shown to the right thereof. The two parallel beam components are focussed at the focal plane 48 by the converging lens 46 to overlap with each other and thereby form an interference pattern, and the objective lens 50 focuses an image of the interference pattern on the retina 56 of the eye 54. The lens 34 may be arranged to focus the parallel beam components at a point other than the focal plane 48 to obtain variable overlapping of the beam components if desired.

In the embodiment shown in FIG. 2, the laser 30 is fixed in position and the spacing between the parallel beam components emerging from the prisms 38 and 40 respectively and thereby the interference fringe spacing can be continuously varied simply by moving the prism 36 along the axis of the laser 30 (right and left). With the prism 36 in the solid line position so that the beam emerging therefrom is spaced from the axis 44 by a distance $S_1$, the beam is split into the beam components as shown by solid arrows and described above. If the prism 36 is moved to a broken line position designated as 36′, the beam emerging therefrom is spaced from the axis 44 by a distance $S_2$. The beam, which in this case is designated by broken arrows, is incident on the upper face of the prism 38 and refracted thereby to be incident on the axis 44 of the material 42 at the same angle B but at a different point. The beam is split into the two components which emerge from the prisms 38 and 40 respectively parallel to the axis 44 as before, but in this case the spacing between the beam components to the left and right of the axis 44 is much greater. Consequently, the fringe spacing is also varied. It will be understood that the spacing between the parallel beam components emerging from the prisms 38 and 40 respectively and thereby the interference fringe spacing is continuously variable over a large range simply by moving the prism 36 along the axis of the laser 30.

Many modifications are possible to the embodiment shown in FIG. 2. For example, the axis of the laser 30 may be parallel to the upstream or upper face of the prism 38, in which case the beam would be incident on the upper face of the prism 38 at a right angle and would not be refracted by the prism 38 before reaching the material 42. Also, the prism 36 may be omitted and the laser 30 movable to directly radiate the beam onto the upper face of the prism 38. With such modifications, it is required only that the beam be incident on the material 42 at the angle B.

Various alternative configurations of the prisms 38 and 40 are shown in FIGS. 4a, 4b and 4c. In FIG. 4a, the prisms 38a and 40a are identical and have a triangular rather than a truncated triangular cross-section with all face angles equal to A. In FIG. 4b, the prism 38b has a triangular cross-section with both face angles equal to A. The prism 40b, however, has a triangular cross-section with the lower face angle equal to A and the upper face angle equal to B. Actually, the upper face angle of the prism 40b may be any value greater than B. In FIG. 4c, the prism 38c has a truncated triangular cross-section with both face angles equal to A. The prism 40c also has a triangular cross-section with the lower face angle equal to A and the upper face angle equal to or greater than B. The beam paths through the various prisms are designated by arrows.

In FIG. 2, the semi-transparent material 42, which may be embodied by a semi-transparent mirror, serves as a beam splitter. The prisms 38 and 40 serve as beam deflecting means. It is well known in the art of optics that a beam may be deflected by reflection rather than refraction. Another embodiment of the present invention is shown in FIG. 3 which makes use of this principle in which the beam deflecting means are plane mirrors rather than prisms.

Figure 3:
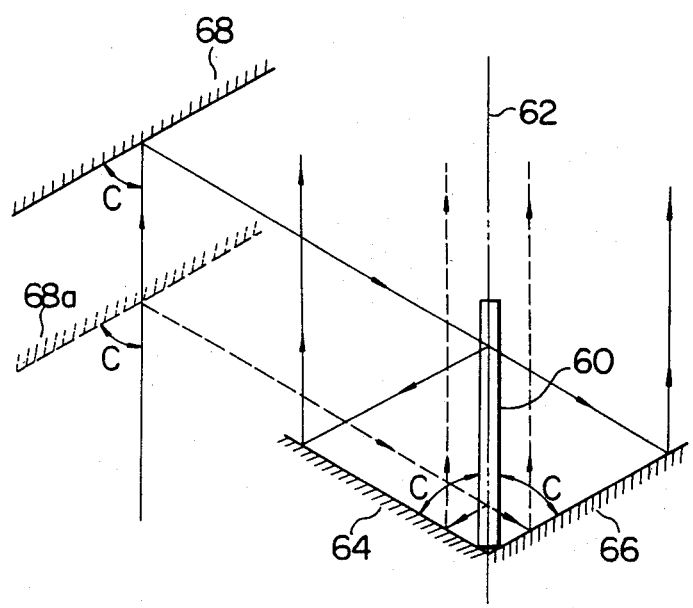
FIG. 3 is a schematic view of another embodiment of the beam splitting apparatus shown in FIG. 2.

In FIG. 3, a plane semi-transparent mirror 60 has a longitudinal axis 62. Plane mirrors 64 and 66 are disposed at the opposite sides of the mirror 60 at an angle C to the axis 62. Another plane mirror 68 is oriented parallel to the mirror 66 and movable parallel to the axis 62. A light beam (the source is not shown) is parallel to the axis 62 and reflected from the mirror 68 onto the mirror 60. With the mirror 68 in the solid line position, the beam travels a path designated by solid arrows. Specifically, the beam is reflected from the mirror 68 onto the mirror 60 which splits the beam into two components in a manner identical to the material 42 of the embodiment of FIG. 2. A first beam component is reflected from the mirror 60 onto the mirror 64 from which the beam component is reflected into a beam path upwards parallel to the axis 62 and to the left thereof.

A second beam component passes through the mirror 60 and is reflected from the mirror 66 into a beam path upwards parallel to the axis 62 and to the right thereof. If the mirror 68 is moved to a broken line position designated as 68a, the operation is the same as that described above except that the spacing between the beam components reflected from the mirrors 64 and 66 respectively is much less to the left and right of the axis 62. In this manner, an incident beam is split into two parallel beams of variable spacing therebetween simply by moving the mirror 68 along a straight line path.

It will be understood that either the combination of the prisms 38 and 40 and the material 42 shown in FIG. 2 or the combination of the plane mirrors 64, 66 and 60 shown in FIG. 3 constitute a novel apparatus for splitting an incident light beam into two parallel components with continuously variable spacing therebetween which is advantageous in numerous industrial applications unrelated to producing an optical interference pattern.

An apparatus for producing an interference pattern embodying the present invention provides the following specific advantages.

1. The apparatus can be easily aligned and calibrated.
2. The apparatus is simple in configuration and easy and inexpensive to construct.
3. The apparatus is highly resistant to vibration, especially the embodiment shown in FIG. 2 which comprises two solid prisms.
4. The loss of light is negligible.
5. The optical components are easily manufactured.
6. The fringe spacing can be easily varied with a single linear movement.
7. The apparatus has stable polarization characteristics.
8. Variation of the fringe spacing does not result in a variation in the intensity of the interference pattern.

What is claimed is:

1. Apparatus for producing an interference pattern of continuously variable fringe spacing, comprising:
    a coherent light beam source;
    a plane semi-transparent reflecting means;
    first and second prisms, the bases of the first and second prisms being parallel to the semi-transparent reflecting means and disposed closely adjacent to the opposite sides thereof, the beam source being arranged to radiate a coherent light beam onto the first prism at an angle so that the coherent light beam is refracted by the first prism so as to be incident on the semi-transparent reflecting means at a predetermined angle and split by the semi-transparent reflecting means into first and second beam components, the first beam component being reflected by the semi-transparent reflecting means and refracted by the first prism into a first beam path parallel to the semi-transparent reflecting means, the second beam component passing through the semi-transparent reflecting means and being refracted by the second prism into a second beam path parallel to the first beam path; and
    beam converging means to converge the first and second beam components to overlap and produce an interference pattern, the beam source being operative to displace the coherent light beam relative to the semi-transparent reflecting means in such a manner that the spacing between the first and second beam paths of the first and second beam components and thereby the fringe spacing are continuously variable.

2. The apparatus according to claim 1, in which the beam converging means comprises a lens.

3. The apparatus according to claim 1, in which the coherent light beam source comprises a laser.

4. The apparatus according to claim 1, further comprising an objective lens arranged downstream of the beam converging means to form an image of the interference pattern.

5. The apparatus according to claim 1, in which the beam source is arranged to radiate the coherent light beam perpendicular to the semi-transparent reflecting means, the apparatus further comprising a plane reflector movable along the axis of the beam source to reflect the coherent light beam onto the first prism at said angle.

6. The apparatus according to claim 1, in which the downstream faces of the first and second prisms are orientated at an equal angle to the opposite sides of the semi-transparent reflecting means.

7. The apparatus according to claim 6, in which the first and second prisms have the same index of refraction.

8. The apparatus according to claim 1, in which the transmittance and reflectance of the semi-transparent reflecting means are equal at said predetermined angle.

9. The apparatus according to claim 1, in which the first prism has a triangular cross-section with equal face angles.

10. The apparatus according to claim 1, in which the first prism has a truncated triangular cross section.

11. The apparatus according to claim 1, in which the first and second prisms are identical.

12. Apparatus for producing an interference pattern of continuously variable fringe spacing, comprising:
    a coherent light beam source;
    a plane beam splitter, the beam source being arranged to radiate a coherent light beam onto the beam splitter at a predetermined angle thereto, the beam splitter splitting the beam into first and second beam components;
    first and second beam deflecting means, the first and second beam components from the splitter being incident on the first and second beam deflecting means respectively, the first and second beam deflecting means deflecting the first and second beam components into first and second beam paths respectively parallel to the beam splitter;
    beam converging means to converge the first and second beam components deflected by the first and second beam deflecting means respectively to overlap and produce an interference pattern;
    the beam source being fixed parallel to the beam splitter, the apparatus further comprising third beam deflecting means movable along the axis of the beam source to deflect the beam onto the beam splitter at the predetermined angle.

13. Apparatus for producing an interference pattern of continuously variable fringe spacing, comprising:
    a coherent light beam source;
    a plane beam splitter, the beam source being arranged to radiate a coherent light beam onto the beam splitter at a predetermined angle thereto, the beam splitter splitting the beam into first and second beam components;
    first and second beam deflecting means, the first and second beam components from the beam splitter being incident on the first and second beam deflecting means respectively, the first and second beam deflecting means deflecting the first and second beam components into first and second beam paths respectively parallel to the beam splitter;

beam converging means to converge the first and second beam components deflected by the first and second beam deflecting means respectively to overlap and produce an interference pattern;

the beam source being fixed perpendicular to the beam splitter, the apparatus further comprising third beam deflecting means movable along the axis of the beam source to deflect the beam onto the beam splitter at the predetermined angle.

14. Apparatus for producing an interference pattern of continuously variable fringe spacing, comprising:

a coherent light beam source;

a plane semi-transparent mirror;

first and second plane mirrors arranged at an equal angle to the opposite faces of the semi-transparent mirror, the beam source being arranged to radiate a coherent light beam onto the semi-transparent mirror at a predetermined angle thereto, the semi-transparent mirror splitting the beam into first and second beam components, the first beam component being reflected by the semi-transparent mirror onto the first plane mirror and the second beam component passing through the semi-transparent mirror onto the second plane mirror, the first and second beam component being reflected by the first and second plane mirrors respectively parallel to the semi-transparent mirror; and beam converging means to converge the first and second beam components to overlap and produce an interference pattern, the beam source being operative to displace the coherent light beam relative to the semi-transparent mirror in such a manner that the spacing between the first and second beam paths of the first and second beam components and thereby the fringe spacing are continuously variable.

* * * * *

UNITED STATES PATENT AND TRADEMARK OFFICE
CERTIFICATE OF CORRECTION

PATENT NO. : 4,009,940
DATED : March 1, 1977
INVENTOR(S) : Hitoshi OHZU

It is certified that error appears in the above–identified patent and that said Letters Patent are hereby corrected as shown below:

In the heading of the Patent, in the line following "Foreign Application Priority Data" change "49-4904809" to -- 49-48039 --.

Signed and Sealed this nineteenth Day of July 1977

[SEAL]

Attest:

RUTH C. MASON
Attesting Officer

C. MARSHALL DANN
Commissioner of Patents and Trademarks